US006788394B1

(12) United States Patent
Garcia-Rubio et al.

(10) Patent No.: US 6,788,394 B1
(45) Date of Patent: Sep. 7, 2004

(54) SPECTROPHOTOMETRIC SYSTEM AND METHOD FOR THE IDENTIFICATION AND CHARACTERIZATION OF A PARTICLE IN A BODILY FLUID

(75) Inventors: Luis Humberto Garcia-Rubio, Temple Terrace, FL (US); Yvette D. Mattley, Tampa, FL (US); German Leparc, Tampa, FL (US); Manuel Bayona, Fort Worth, TX (US); Andres Cardenas, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/249,637

(22) Filed: Apr. 28, 2003

Related U.S. Application Data

(63) Continuation of application No. 09/904,107, filed on Jul. 12, 2001, now abandoned, which is a continuation-in-part of application No. 09/861,781, filed on May 21, 2001, which is a division of application No. 09/206,630, filed on Dec. 7, 1998, now abandoned, which is a continuation-in-part of application No. 08/775,645, filed on Dec. 31, 1996, now abandoned, which is a continuation-in-part of application No. 08/385,717, filed on Feb. 8, 1995, now Pat. No. 5,589,932.

(60) Provisional application No. 60/217,742, filed on Jul. 12, 2000.

(51) Int. Cl.[7] .............................................. G01N 33/48

(52) U.S. Cl. ........................ 356/39; 600/310; 600/314
(58) Field of Search ................................ 356/335, 337, 356/441, 39, 433, 300–334; 600/310, 314, 322

(56) References Cited

U.S. PATENT DOCUMENTS

| 4,832,483 A | * | 5/1989 | Verma ........................ 356/39 |
| 5,432,061 A | * | 7/1995 | Berndt et al. ................ 435/34 |
| 5,991,653 A | * | 11/1999 | Richards-Kortum et al. ..... 600/475 |

* cited by examiner

*Primary Examiner*—Richard A. Rosenberger
*Assistant Examiner*—Vincent P. Barth
(74) *Attorney, Agent, or Firm*—Smith & Hopen, P.A.; Anton J. Hopen; Molly L. Sauter

(57) ABSTRACT

An infectious disease or disorder in a fluid, such as a mammalian blood sample, is detected by taking a transmission spectrum of a test sample in at least a portion of the ultraviolet visible near-infrared and comparing the spectrum with a standard sample spectrum. From the comparison it is then determined whether the fluid from the test sample contains an infectious disease or disorder, and an identity of the infectious disease or disorder is determined. Spectroscopic and multiwavelength turbidimetry techniques provide a rapid, inexpensive, and convenient means for diagnosis. The comparison and determination steps may be performed visually or by spectral deconvolution.

28 Claims, 7 Drawing Sheets

FIG. 7

| Table 1. Malaria Patient Information ||||||
|---|---|---|---|---|---|
| Malaria Patient | Species | Symptoms Noted | Diagnosed | Treated | Spectroscopy |
| 1 | F | day 1 | day 10 | 7 days | day 17 |
| 2 | F | day 1 | no data | no data | day 17 |
| 3 | V | day 1 | day 4 | 4 days | day 17 |
| 4 | Suspected | no data | no data | no data | day 17 |

FIG. 8

| Table 2. Dengue Fever Patient Information ||||||
|---|---|---|---|---|---|
| Dengue Fever | Type | Symptoms | Clinic Diagnosis | Laboratory Diagnosis | Spectroscopy |
| 1 | H | day 1 | day 5 | no data | day 21 |
| 2 | C | day 1 | day 2 | day 4 | day 7 |
| 3 | C | day 1 | day 3 | day 6 | day 19 |
| 4 | C | day 1 | day 3 | no data | day 30 |

SPECTROPHOTOMETRIC SYSTEM AND METHOD FOR THE IDENTIFICATION AND CHARACTERIZATION OF A PARTICLE IN A BODILY FLUID

CROSS-REFERENCE TO RELATED APPLICATIONS

This application is a continuation of U.S. application Ser. No. 091904,107, filed Jul. 12, 2001 now abandoned, which claims priority from commonly owned provisional application Ser. No. 60/217,742, filed Jul. 12, 2000, the disclosure of which is incorporated herein by reference. This application is also a continuation-in-part of co-pending U.S. application Ser. No. 09/861,781, filed May 21, 2001, which is a divisional of U.S. application Ser. No. 09/206,630 filed Dec. 7, 1998 now abandoned, which is a continuation-in-part of U.S. application Ser. No. 08/775,645 filed Dec. 31, 1996 now abandoned, which is a continuation-in-part of U.S. application Ser. No. 08/385,717 filed Feb. 8, 1995, now U.S. Pat. No. 5,589,932 issued on Dec. 31, 1996.

BACKGROUND OF INVENTION

1. Field of the Invention

The present invention relates to a spectroscopic system and methods for the identification and characterization of particles in a fluid, and, more particularly, to such systems and methods for the identification and characterization of particles in a bodily fluid.

2. Description of Related Art

A critical limitation in the area of disease identification, diagnosis, and prevention has been the lack of simple, rapid, and effective screening techniques. This problem is particularly acute in locations and/or situations where rapid analysis and diagnosismay involve decisions concerning life-threatening circumstances such as natural disasters or combat, and where the need for portable laboratories is accentuated by the remoteness of areas where diseases are endemic and where epidemics are generated. In addition, in the medical field there is a considerable need for the identification of markers that permit the diagnosis and treatment of diseases early in their development stage and thus avoid lengthy periods of incubation, which invariably worsen the condition of the patient.

Typically, microorganisms and viruses of concern have sizes ranging between 0.5 and 20 $\mu$pm and, in many cases, are present in fairly dilute concentrations. Although the analytical instrumentation used in medical and clinical laboratories has improved considerably over the past decade to the present, there are still no suitable techniques capable of detecting, classifying, and counting microorganisms in bodily fluids.

Technology known in the art requires that the presence of target microorganisms be detected using microscopy and/or immunoassay techniques. These require a significant amount of time, trained technicians, and well-equipped laboratory facilities.

The costs associated with current laboratory techniques for disease identification and diagnosis therefore further accentuate the need for the development of rapid screening methods.

Another limitation of the currently employed technology is a lack of on-line capability and continuous measurement capabilities for the characterization of blood and other fluid components, as well as a lack of portable instrumentation capable of detecting, counting, and classifying specific blood and other fluid components. The problem of portable instrumentation and suitable methods of analysis and diagnosis is particularly relevant to the medical industry, where the need for rapid analysis and diagnosis often involves life-threatening situations. Although the analytical instrumentation used in medical and clinical laboratories has improved considerably over the past decade, there are still no suitable techniques capable of detecting, classifying, and counting on-line critical cell populations and/or pathogens in blood and other bodily fluids.

Blood cell component counting technology known in the art uses, for example, red cell counts, platelet counts, and white cell counts as indicators of the state of disease. White blood cells can be difficult to count if they are present in small numbers. At present automated hematology analyzers that employ light scattering or impedance techniques are used, but these can introduce a high error rate when determining counts for low sample numbers. In cases of leuko-reduced blood products with lower numbers of white blood cells, staining and microscopy or flow cytometry are typically used.

As is known from spectroscopy theory, a measure of the absorption of the attenuation of light through a solution or a suspension is the extinction coefficient, which also provides a measure of the turbidity and transmission properties of a sample. Spectra in the visible region of the electromagnetic spectrum reflect the presence of metal ions and large conjugated aromatic structures and double-bond systems. In the near-ultraviolet (uv) region small conjugated ring systems affect absorption properties. However, suspensions of very large particles are powerful scatterers of radiation, and in the case of cells and microorganisms, the light scattering effect can be sufficiently strong to overwhelm absorption effects. It is therefore known to use uv/vis spectroscopyto monitor purity, concentration, and reaction rates of such large particles and their suspending media.

Many attempts have been made to estimate the particle size distribution (PSD) and the chemical composition of suspended particles using optical spectral extinction (transmission) measurements. However, previously used techniques neglect the effects of the chemical composition and require that either the form of the P80 be known a prioii or that the shape of the PSD be assumed. One of the present inventors has applied standard regularization techniques to the solution of the transmission equation and has demonstrated correct PSDs of a large variety of polymer lathces, protein aggregates, silicon dioxide and alumina particles, and microorganisms.

It has also been known to use the complementary information available from simultaneous absorption and light scattering measurements at multiple angles for the characterization of the composition and molecular weight and shape of macromolecules and suspended particles (Garcia-Rubio, 1993; and U.S. Pat. No. 5,808,738, the disclosure of which is incorporated herein by reference).

Interferometric techniques are known in the art for cell classification (Cabib et at., U.S. Pat. Nos. 5,991,028 and 5,784,162) which use fluorescence microscopy with stained cells. Fluorescence and reflection spectroscopy can also be used to characterize a material by sensing a single wavelength (Lemelson, U.S. Pat. Nos. 5,995,866; 5,735,276; and 5,948,272), which can detect organisms in a bodily fluid. Electroluminescence may also be used to detect an analyte in a sample (Massey et at., U.S. Pat. No. 5,935,779). Cell counting may be accomplished by vibrationalspectroscopy (Zakim et al. U.S. Pat. No. 5,733,739). Infrared techniques can detect cellular abnormalities (Cohenford et al., U.S. Pat. Nos. 6,146,897 and 5,976,885; Sodickson et al., U.S. Pat. No. 6,028,311).

One of the present inventors previously developed ultraviolet-visible spectroscopic techniques for detecting and classifying microorganisms in water (Garcia Rubio, U.S. Pat. No. 5,616,457), for characterizing blood and blood types (Garcia Rublo, U.S. Pat. No. 5,589,932), and, as mentioned above, for characterizing particles with a multiangle-multiwavelength system (Garcia-Rubio et at., U.S. Pat. No. 5,808,738). The disclosures of these patents are incorporated herein by reference.

SUMMARY OF INVENTION

It is therefore an object of the present invention to provide a system and method for identifying and diagnosing an infectious disease.

It is a further object to provide such a system and method for identifying and diagnosing such an infectious disease in the bloodstream.

It is another object to provide such a system and method for identifying and diagnosing such an infectious disease in another bodily fluid.

It is an additional object to provide such a system and method for identifying and diagnosing a blood disease.

It is yet a further object to provide such a system and method for identifying and diagnosing a disease that affects the size, shape, and/or chemical composition of a particulate or other component in a bodily fluid.

It is yet another object to provide such a system and method that are operable in a remote location.

These and other objects are achieved by the present invention, a method for detecting a presence of and identifying an infectious disease or disorder in a mammalian blood sample. Herein the word disorder is intended in its broadest sense, that is, as any abnormality detectable over a known range of characteristics of the measured particulates or suspending medium.

The method comprises the steps of taking a multiwavelength spectroscopy measurement, typically a transmission spectrum of a test blood sample in at least a portion of the ultraviolet visible near-infrared range of the electromagnetic spectrum and comparing the spectrum with a standard blood sample spectrum known to be free from the infectious disease or disorder. From the comparison it is then determined whether the blood from the test sample contains the infectious disease or disorder, and an identity of the infectious disease or disorder is determined.

Spectroscopic and multiwavelength turbidimetry techniques provide a rapid, inexpensive, and convenient means for diagnosis. As a first embodiment, the comparison and determination steps may be performed visually, since the signatures of certain diseases and disorders are so strong; in another embodiment it has been found that the spectral deconvolution of the turbidimetric spectra can provide additional and more detailed qualitative and quantitative information. Both embodiments of the invention can rapidly and inexpensively achieve disease diagnosis in remote locations and at a natural disaster, epidemic, or combat site.

In a particular subembodiment, a change in a blood particle or other component caused by an infectious agent or disorder is detected spectroscopically. Such a change may comprise, for example, a shape change, such as occurs with sickle cell anemia, or a lysis, for example, of a red blood cell, which releases free hemoglobin and bilirubin into the blood plasma.

In another subembodiment the test sample may comprise another bodily fluid for detecting a presence of an infectious disease or disorder.

The method is based on multiwavelength spectroscopy measurements and the interpretation of the absorption and scattering properties of single particles from a plurality of populations and their suspending media. The spectroscopy measurements may comprise transmission, reflectance, and multiangle multiwavelength, using either polarized or unpolarized light, in the uvvisnear-infrared portions of the electromagnetic spectrum. Unlike microscopy measurements, the samples typically comprise cells in the range of 106 particles. The analytical method yields such information as, but not intended to be limited to, particle counts, compositional analysis, size, and shape of the particulates and the suspending media.

The invention is believed to provide a multiplicity of improvements over the prior art in achieving a rapid, inexpensive, and convenient means for characterization and detection of particulates in a bodily fluid, including characterization of such particulates as, but not intended to be limited to, cell shapes, blood antigens, microorganisms, and viruses. The rapidity and portability of the system of the invention permits its use in critical conditions such as epidemics and combat and also in remote and/or technology-disadvantaged locations.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF DRAWINGS

FIG. 7 is table 1 which provides accompanying malaria diagnosis data provided by the Laboratorio Regional de Apoyo Epidemiologica, Valencia, Venezuela.

FIG. 8 is table 2 which provides accompanying dengue fever diagnosis data provided by the Laboratorio Regional de Apoyo Epidemiologica, Valencia, Venezuela.

DETAILED DESCRIPTION

A description of the preferred embodiments of the present invention will now be presented with reference to FIG. 18.

The system of the present invention comprises any of known standard spectrometers, such as a portable fiber optics-based spectrophotometer for laboratory testing, in situ measurements, and field applications. The spectrophotometer should be capable of recording the transmission, reflectance, or angular backscattering spectra of blood and other bodily fluids, neat, in solution, and in situ, in any combination or portion of the ultraviolet, visible, and near-infrared portions of the electromagnetic spectrum, preferably with a resolution of at least 2 nm. Recent developments in miniature spectrometer technology permit the use of portable multiprobe integrated systems for rapid blood characterization and diagnosis within the scope of the present invention.

Figure 1:
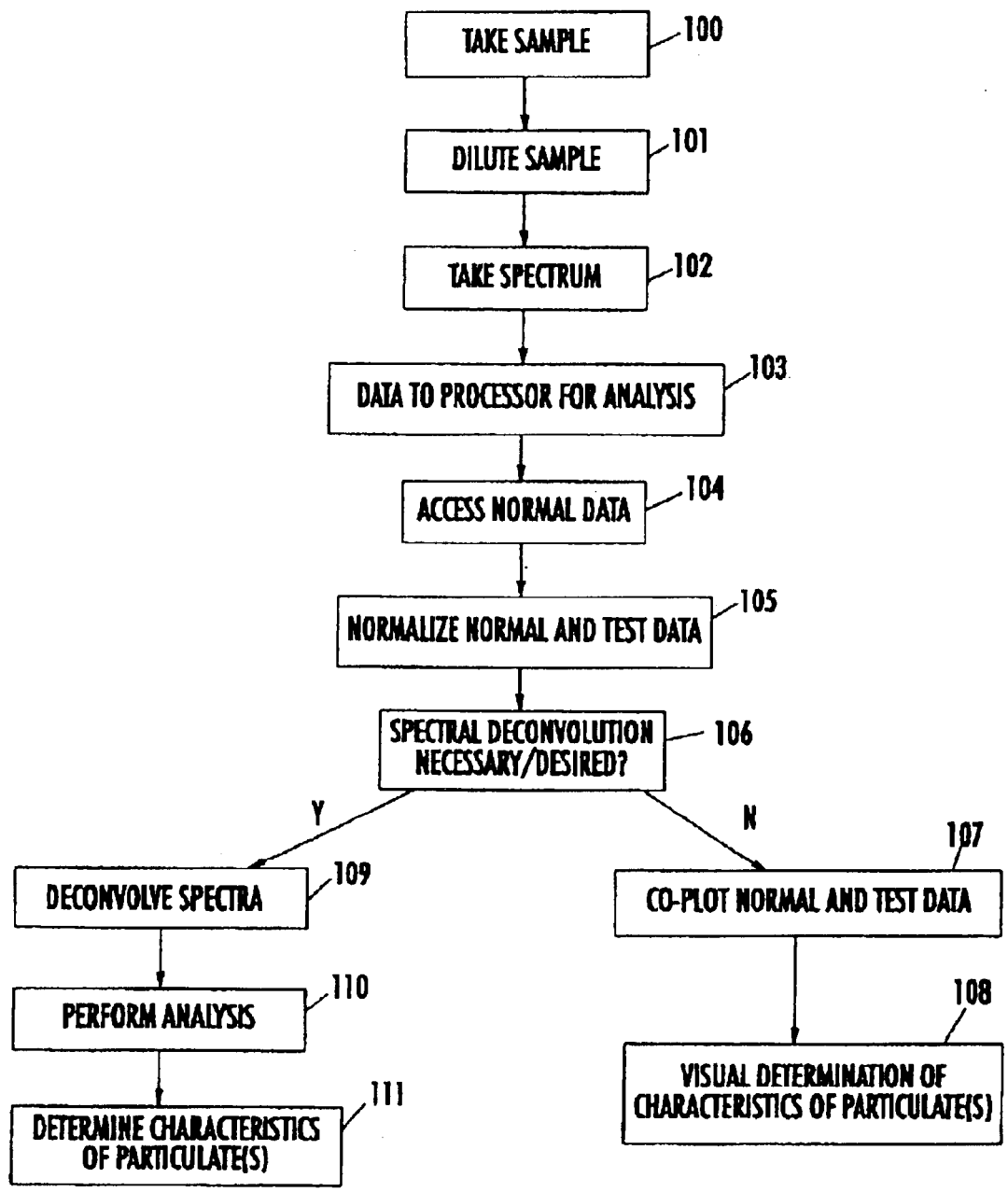
FIG. 1 is a flow chart of the method of the present invention.

An exemplary method of analyzing a fluid sample for the presence of particulates, their characteristics, and that of the suspending medium is shown in the flow chart of FIG. 1. A sample, such as a blood sample, is taken (block 100) and diluted (when appropriate) (block 101) to a concentration level for spectrophotometer linearity, typically 4000 cells per microliter for whole blood. This number is not intended as a limitation, and it will be understood by one of skill in the art that such values are likely to change with the introduction and alteration of technology in the field. An exemplary figure for use at present comprises 1.5 Au.

A exemplary blood dilution protocol is followed for the detection of, for example, a tropical disease, which comprises drawing a whole blood sample into an anticoagulantand diluting substantially 1:1000 with physiological saline. One dilution tube for each whole blood sample that is to be analyzed is prepared by pipetting 3 mL of saline into the tube and adding 3 pL blood, after wiping the outside of the pipette tip to remove excess whole blood. The sample is mixed by inverting the cuvette gently three times.

If dilution tubes are not available, the whole blood can be diluted directly into a cuvette by adding 2 pL whole blood into 2 mL saline in the cuvette. Alternatively, the sample can be placed in a thin measurement cell such that the complete transmission spectrum can be recorded in accordance with known spectroscopy practices.

If the diluted sample is above 1.5 absorbance units in the spectral region measured from 240 to 800 nm, an additional 0.5 mL saline should be added directly to the cuvette and mixed by inverting gently three times. If the spectrum is still too strong, repeat the saline addition until the spectrum is below 1.5 absorbance units. Alternatively, if the spectrum is too concentrated (above 1.5 absorbance units), a new whole blood dilution can be prepared by using less whole blood (e.g., 2 pL whole blood into 3 mL saline).

If the diluted blood sample is below 0.2 absorbance units in the spectral region measured from 240 to 800 nm, prepare a new whole blood dilution using more whole blood (e.g., 4 ii whole blood in 3 mL saline). Similar effects can be accomplished by adjusting the path length of the measurement cell in accordance with standard spectroscopy practices.

In a particular embodiment, the cuvette should be rinsed five times with deionized water before measuring the spectrum of another diluted blood sample.

After all the samples have been analyzed each day, the cuvette should be cleaned by filling it with a dilute soap solution and sonicating for 10 mm. After sonication, rinse the cuvette ten times with deionized water to remove residual soap. The cuvette should be stored with deionized water in it.

A transmission spectrum of the sample properly diluted relative to the path length used sample is taken (block 102) with the spectrophotometer, and the data collected are sent to a processor (block 103), wherein standard data from normal controls are resident and may be accessed (block 104). The test and standard data are then normalized (block 105) so that they may be more easily compared. In some cases normalization may not a necessity. The differences are significant enough without normalization.

If the characteristic being examined for has a sufficiently strong signature within the spectrum (block 106), the spectra may be co-plotted (block 107) and a visual determination made (block 108) for the presence of the characteristic. The disease-specific spectral features arise from changes in the size, shape, and chemical composition of the major blood components (blood cells and plasma) caused by the pathogen.

If the characteristic does not have strong signal, or if particular features are desired to be calculated, such as particle size distribution, size, shape, or chemical composition (block 106), spectral deconvolution is performed (block 109), an analysis of the deconvoluted data performed (block 110), and the characteristic of the particulate(s) determined (block 111). This information is used to define elements of classification for the quantification of chemical species, cell enumeration, and the identification of viruses, bacteria, or protozoa of interest, for example, although these are not intended as limitations.

The deconvolution may be accomplished by, for example, calibration based on correlation or with the use of theoretical models based on theories of absorption and scattering of electromagnetic radiation. References authored by some of the present inventors contain disclosure on the analysis of multiwavelength spectroscopic data, and these references are incorporate herein by reference (Brandolin et al., 1991; Chang et aL, 1993; Elicabeetai, 1988, 1990; Garcia-Rubioetai, 1984, 1985, 1987, 1989, 1992, 1993, 1994, 1999; Marquezetal., 1993; Mattley et at., 2000).

As examples, samples may be analyzed for the concentration of several types of hemoglobin, the level of oxygenation, bilirubin, and total hematocrit. It is also possible to identify and classify blood types using their spectral signature and to detect free hemoglobin and other particles present in blood such as abnormal sickling hemoglobin and Plasmodium sp. It will also be possible, it is believed, to detect markers of other diseases such as HIV and HBV.

The uv-vis transmission spectra of a large variety of blood samples of different types have been spectroscopically investigated. These spectra have shown that the uv-vis portion of the spectrum contains sufficient information for the statistical identification and classification of blood types and the subsequent identification of blood diseases and the presence of foreign microorganisms. In addition, the spectra establish the reproducibility of the method, permit identification of spectral features associated with healthy blood, and establish appropriate controls for comparison purposes.

Sample spectra of several blood diseases are shown in FIG. 26, with contrasting spectra for normal controls. FIG. 7 and FIG. 8 display tables 1 and 2 which provide accompanying diagnosis data provided by the Laboratorio Regional de Apoyo Epidemiologica, Valencia, Venezuela, where the malaria and dengue fever data were obtained.

Figure 2:
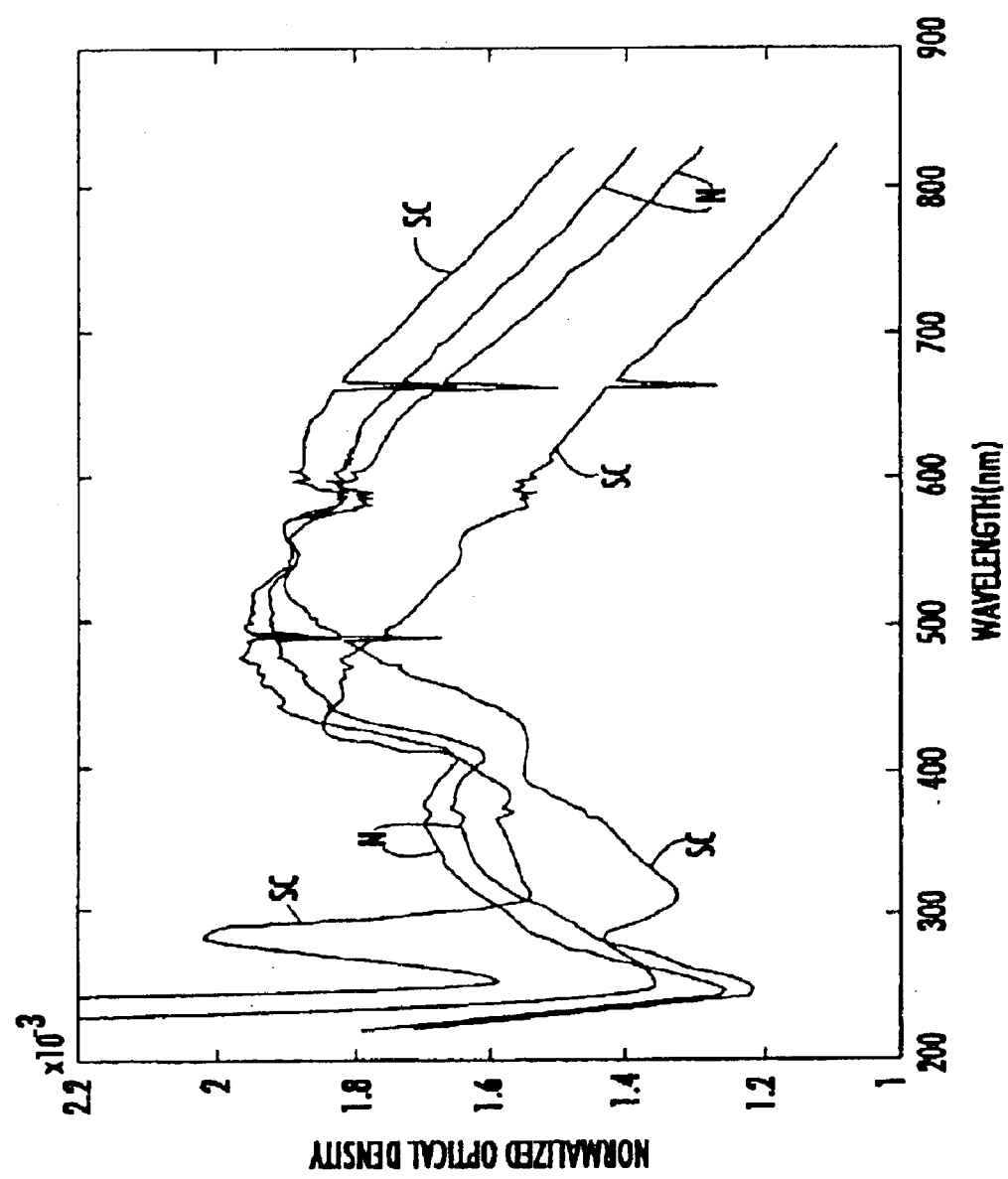
FIG. 2 is an exemplary optical density spectrum for normal and sickle cell red blood cells.

In FIG. 2 are uv-vis spectra of two replicate measurements of normal (N) whole blood together with measurements of whole blood containing sickle cells (SC) from two different patients. Dramatic differences may be noted in the spectral region between 220 and 600 nm, where the main chromophoric groups in blood, including nucleic acids, proteins, and liganded metals, are known to absorb. The spectral differences between 600 and 900 nm are also significant in that they reflect changes in the scattering characteristics (size and shape) of the cells. Thus this region of the electromagnetic spectrum is particularly suitable for the detection and identification of particulate(s) with a high degree of specificity.

Figure 3:
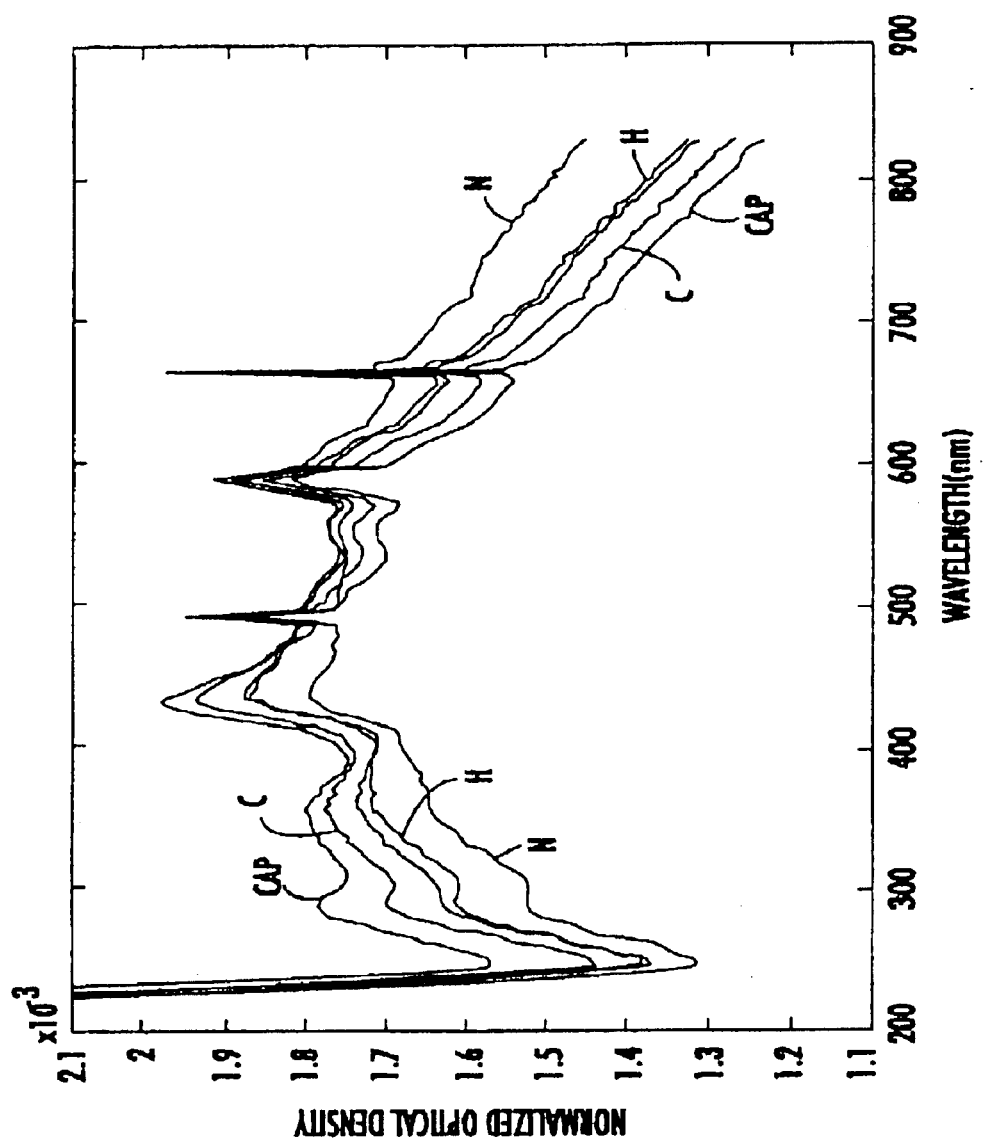
FIG. 3 is an exemplary optical density spectrum for normal and dengue fever patients.

In FIG. 3 spectra of normal (N) whole blood and whole blood from dengue fever patients are shown. The dengue fever patients include hemorrhagic (H), classical acute phase (CAP), and classical (C). Again dramatic differences are shown across the uv-vis spectrum, and there are clear similarities in the absorption and scattering characteristics of the spectra from dengue fever patients' blood. One may also distinguish a patient in the acute phase of the disease.

Figure 4:
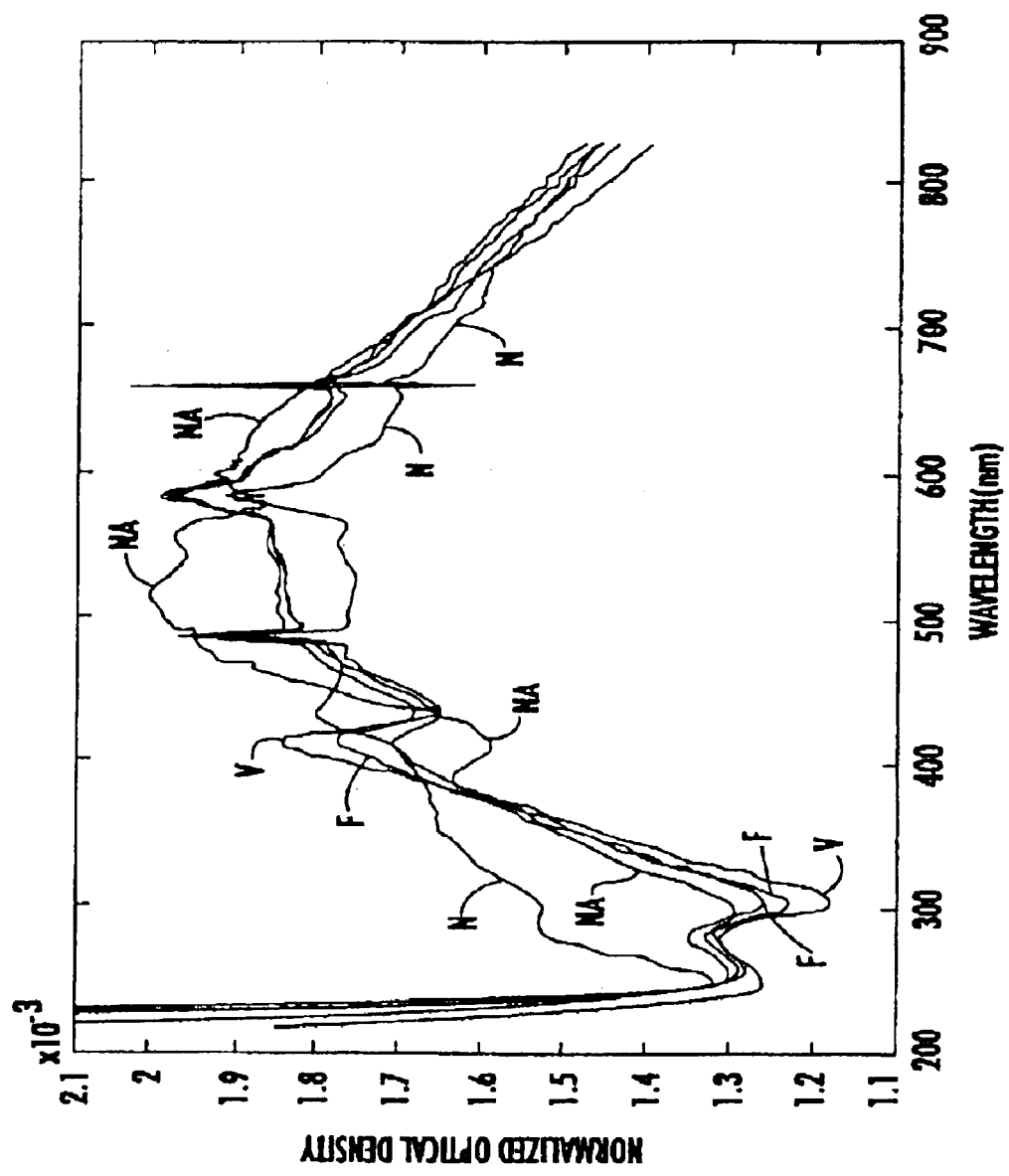
FIG. 4 is an exemplary optical density spectrum for normal and malarial patients.

In FIG. 4 are shown spectra of normal (N) whole blood, aged normal (NA) whole blood, and blood from malarial patients. Dramatic differences in the spectral region between 250 and 600 nm are shown; as above, the changes in the 600–900 nm range are significant in that they reflect changes in the scattering characteristics of the cells. In malarial patients this is to be expected, since it is known that malarial parasites host in red blood cells. There are also clear spectral differences between the two types of malarial parasites, Vivax (V) and Falciparum (F). It is also notable that the age of the blood sample has a clearly discernible effect on the spectra.

From FIG. 24 it may be seen that the system and method of the present invention are capable of identifying and classifying blood-borne diseases. A penetration level, that is, a level of infection, may also be deduced from the magnitude of the signature, which can be seen in FIG. 2, as an example.

Figure 5:
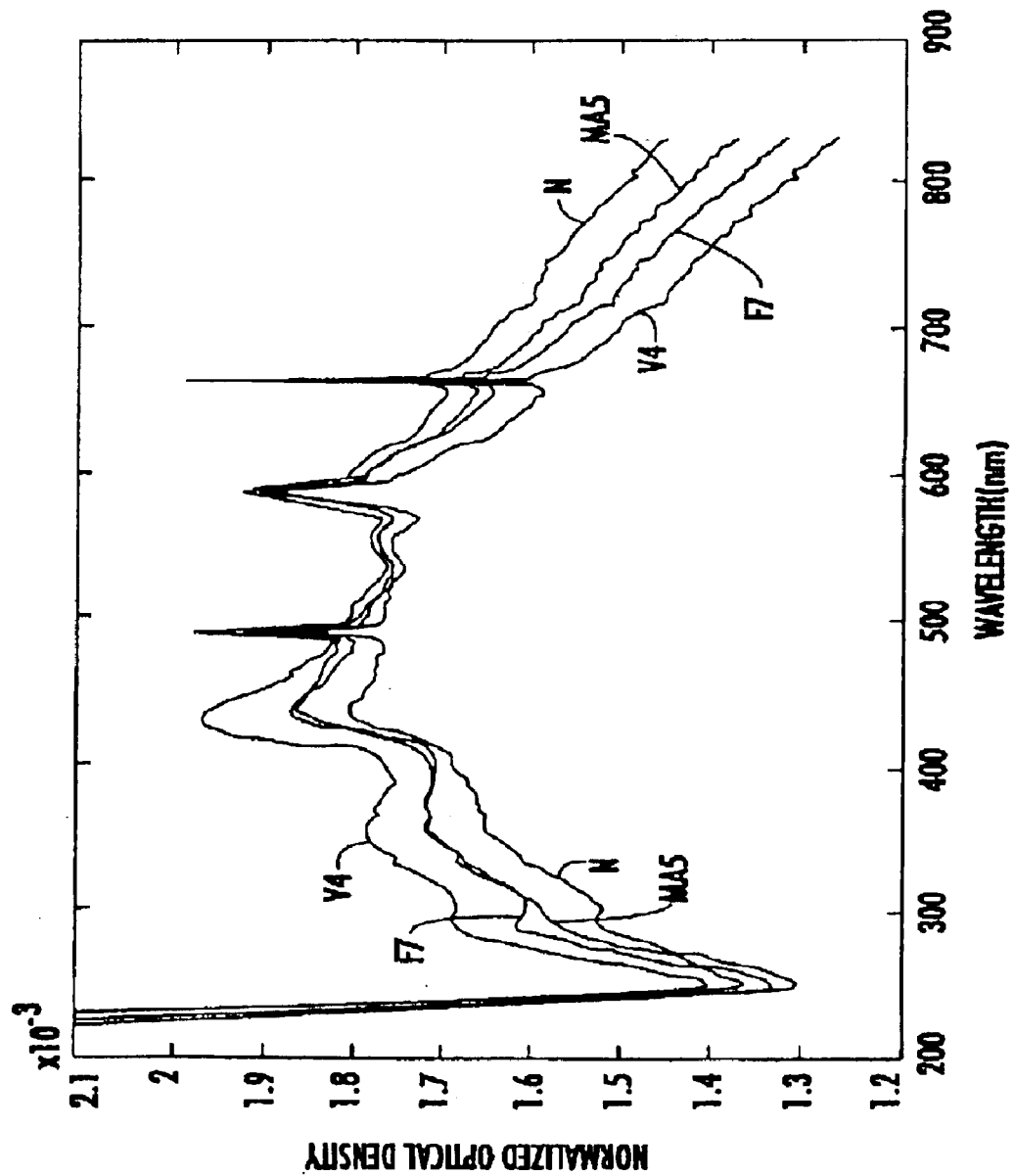
FIG. 5 is an exemplary optical density spectrum for normal and treated malarial patients.

The effect of treatment on the spectrum of whole blood for malarial patients is shown in FIG. 5. The spectra include normal (N), Falciparum treated 7 days (F7), Vivax treated 4 days (V4), suspected malaria and amebiasis treated for 5 days with antibiotics (MA5). Referring back to FIGS. 3 and 4, it may be seen that, as the disease is treated, the spectral characteristics of the blood begin to approach those of normal whole blood.

Thus it may be seen that the present invention can be used to monitor both the extent of the disease and the progress of the treatment.

Figure 6:
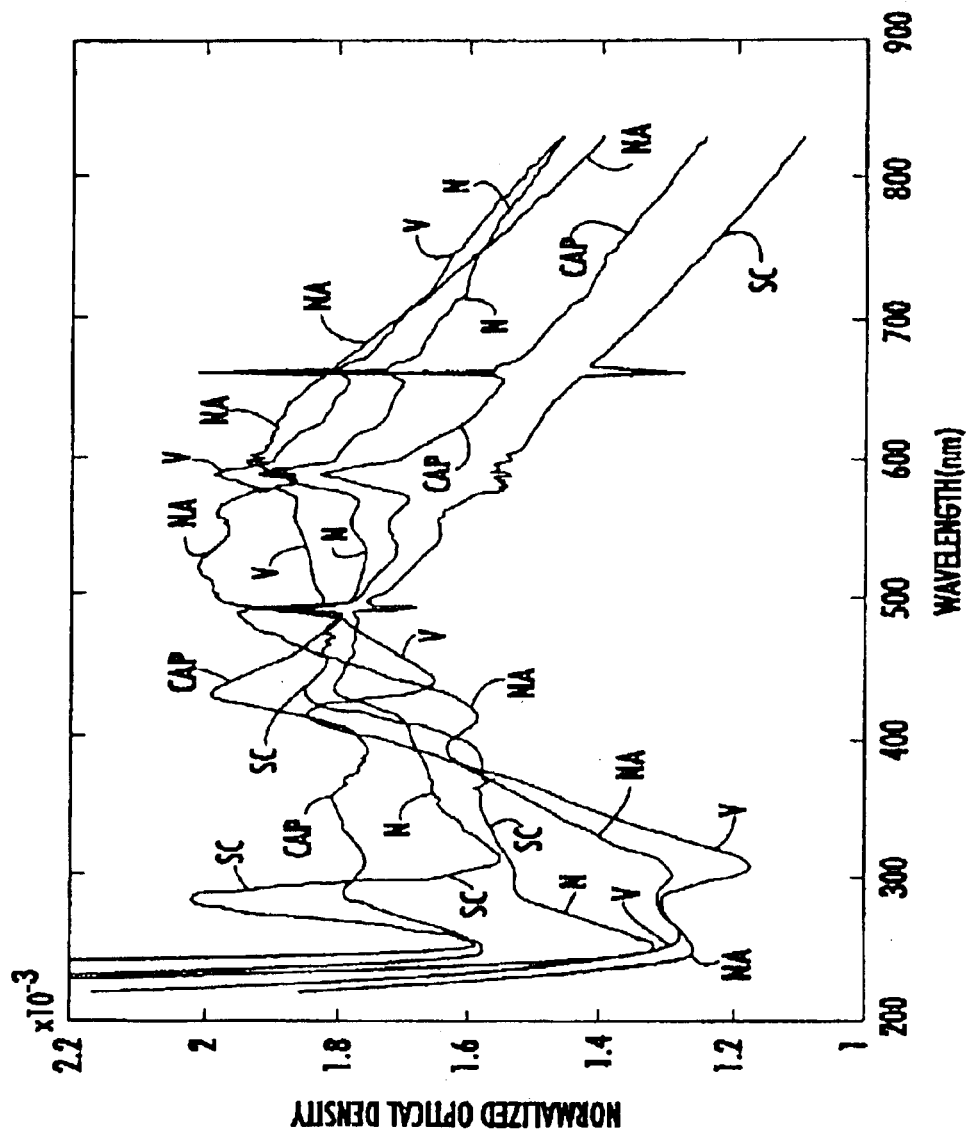
FIG. 6 is an exemplary optical density spectrum for normal, aged, sickle cell, and malarial patients.

Representative samples of fresh healthy whole blood (N), healthy blood aged 6 days (NA), whole blood containing sickle cells (SC), and whole blood from individuals diagnosed with Vivax malaria (V), and dengue fever in the classical acute phase (CAP) are plotted together in FIG. 6 for comparison.

It should be noted that the system and method can also be applied to other bodily fluids or tissues in the diagnosis of syphilis, gonorrhea, HIV, tuberculosis, and onchocerciasis, and for the characterization of micrometer- and submicrometer-sized particles such as may be present in blood and other bodily fluids, such as, but not intended to be limited to, mucus, urine, tear fluid, spinal fluid, menstrual fluid, and amniotic fluid. In spinal fluid, for example, meningitis, both viral and bacterial, would be easily detectable; in urine, microalbuminemia or hyperproteinurea can be detected to suggest a diagnosis of kidney disease.

It is believed that the present invention provides a maximum amount of information and also the greatest sensitivity of detection and identification. Samples in a range of 106 particles are being examined simultaneously, and are not merely being counted, as with microscopic methods.

Another advantage of the present invention is speed of analysis. Blood testing by microscopy typically entails a one-week waiting time and requires a trained microscopist to interpret the data. The present invention provides an immediate analysis, which means that treatment can begin immediately, and the patient does not have to make a return trip to the doctor office. Further, the speed of analysis permits on-site use in remote locations and in critical situations such as combat and in an epidemic.

A further advantage of the present invention is the cost. Whereas testing for some disorders or diseases can cost approximately $700, it is believed that the present invention can decrease this amount by two orders of magnitude, owing to lower equipment investment and elimination of the need for highly trained personnel. A laptop computer can accommodate the software required for the system, and a fiber-optic spectrometer is sufficient for data collection. This enables on-site analysis in remote, underdeveloped areas.

In another embodiment of the present invention, the technique of uv-vis spectroscopy is applicable to noninvasive measurements, wherein the absorption, scattering, and polarization properties of the bodily fluid may be studied through the skin.

In yet another embodiment, commercially available metallic beads can be coated with a substance, which will aggregate together if an antibody to the substance exists in the system. Such an aggregation is easily detected with the system and method of the present invention, which can thus be used to test with an immobilized reagent.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

References

Brandolin, A., L. H. Garcia-Rubio, T. Provder, M. E. Kohier, and C. Kuo, "Latex ParticleSize Distribution from Turbidimetry Using Inversion Techniques, Experimental Validation, "ACS Symposium Series No. 472, Chap. 2, 1991.

EliÃ§abe, G., and L. H. Garcla-Rubio, "Latex Particle Size Distribution from Turbidimetry using a Combination of Regularization Techniques and Generalized Cross Validation, "Advances in Chemistry Series Vol. 227, Chap. 6, ACS, Washington D.C., 1990.

Garcia-Rubio, L. H., "The Effect of the Molecular Size on the Absorption Spectra of Macromolecules, "Macmmolecules 20, 3070, 1987.

Garcla-Rubio, L. H., "Determination of the Absorption Coefficient of Proteins in the Presence of Protein Aggregates using Turbimetry, "Chem. Eng. Comm. 80, 193, 1989.

Garcla-Rubio, L. H., "Refractive Index Effects on the Absorption Spectra of Macromolecules, "Macromolecules 25, 2608–13, 1992.

Garcia-Rubio, L. H., C. A. Garcia, and S. Grossman, "Spectroscopy Characterization of Proteins: Use of Model Molecules for Porcine Somatotropin Analysis, "Chem. Eng. Comm., 122, 85–101, 1993.

Garcia-Rubio, L. H., and N. Ro, "Detailed Copolymer Characterization using Ultraviolet Spectroscopy, "Can. J. Chem. 63, 253, 1985.

Garcia-Rubio, L. H., N. Ro, and R. D. Patel, "UV Analysis of Benzoyl Peroxide Initiated Polymerizations and Copolymerizations, "Macromolecules 17, 1998, 1984.

Garcia-Rubio, L. H., J. D. Rose, M. C. Callahan, and R. Robertson, "Combined Absorption and Light Scattering Methods for the Characterization and Detection of Ciyptosporidium, "submitted.

Koumanoti, I., L. Davis, S. Chang, and L. H. Garcia-Rubio, "Spectroscopy Analysis of Particle Suspensions, "Development of Non-Renewable Resources: Challenges and Solutions, Eds, H. El-Shall, A. Ismail, and B. Moudgil. United Engineering Foundation, Inc., New York, pp 83–93, 1999.

Marquez, E., V. R. Bhethanabotla, and L. H. Garcia-Rubio, Macromolecules 26, 479, 1993.

Mattley, Y., G. Leparc, R. Potter, and L. H. Garcia-Rubio, "Light Scattering and Absorption Model for the Quantitative Interpretation of Human Platelet Spectral Data, "Photochem. Photobiol. 71(5), 610–19, 2000.

Throckmorton, J. F., R. Potter, and. L. H. Garcla-Rubio, "Determining a UVNIS Model for Tyrosine: Use of Model Molecules for the Spectroscopy Characterization of Proteins, "Presented at the 5th Symposium: Technologies on Protein Studies and Purification, Grenoble, France, Mar. 17th–19th, 1992.

What is claimed is:

1. A method for detecting a presence of and identifying an infectious disease or disorder in a mammalian blood sample comprising the steps of:
    taking a transmission spectrum of a test blood sample in at least a part of the ultraviolet—visible-near-infrared range of the electromagnetic spectrum;
    comparing the spectrum with a standard blood sample spectrum known to be free from the infectious disease or disorder; and
    determining from the comparison whether the blood from the test sample contains the infectious disease or disorder and an identity of the infectious disease or disorder.

2. The method recited in claim 1, wherein the infectious disease comprises an agent that alters at least one of a shape, a size, and a chemical composition of a normal blood component.

3. The method recited in claim 1, wherein the comparing step comprises identifying a difference in at least one of a peak height, a peak presence, and a slope between the standard sample and the test sample.

4. The method recited in claim 1, wherein a difference between the standard sample and the test sample represents at least one of a presence of free hemoglobin in the test sample; a change in a shape of at least some of the red blood cells; and a change in distribution among blood components.

5. The method recited in claim 1, wherein the transmission spectrum has a resolution of at least 2 nm.

6. The method recited in claim 1, wherein the comparing step comprises identifying a feature of the standard spectrum known to change in a presence of the infectious disease or disorder and the determining step comprises analyzing the test spectrum for a change in the identified feature.

7. The method recited in claim 1, further comprising the step, prior to the comparing step, of normalizing the standard spectrum and the test spectrum for facilitating the comparing step.

8. The method recited in claim 1, further comprising the step, prior to the spectrum taking step, of diluting the blood sample in a physiological saline solution to a concentration of approximately 4000 red blood cells per microliter.

9. The method recited in claim 1, further comprising the step, prior to the spectrum taking step, of diluting the blood sample in a physiological saline solution to a concentration wherein the transmission spectrum reads in a range of approximately 1.5 absorbance units.

10. The method recited in claim 1, further comprising the step, of adjusting a path length in the spectrum taking step to an optical density range in which the response of the spectrometer is substantially linearly related to the concentration of the sample.

11. A method of quantifying a substance in a mammalian blood sample comprising the steps of:
    taking a transmission spectrum of a test blood sample in at least a portion of the ultraviolet visible near-infrared range of the electromagnetic spectrum;
    deconvolving the spectrum into absorption and scattering components; and
    determining from the deconvolution a presence and a concentration of a substance in the blood sample.

12. The method recited in claim 11, wherein the substance is selected from a group consisting of red blood cells, white blood cells, viruses, bacteria, protozoa, and platelets.

13. The method recited in claim 11, wherein the spectrum taking step comprises taking a spectrum in a range of approximately 220–900 nm.

14. The method recited in claim 11, wherein the deconvolving step comprises utilizing a calibration approach based on correlation.

15. The method recited in claim 11, wherein the deconvolving step comprises utilizing absorption and scattering theories.

16. A method for detecting a presence of and identifying an infectious disease or disorder in a mammalian fluid sample, the method comprising the steps of:
    taking a transmission spectrum of a test fluid sample in at least a portion of the ultraviolet visible near-infrared range of the electromagnetic spectrum;
    comparing the spectrum with a standard fluid sample spectrum known to be free from the infectious disease or disorder; and
    determining from the comparison whether the fluid from the test sample contains the infectious disease or disorder and an identity of the infectious disease or disorder.

17. The method recited in claim 16, wherein the fluid sample is selected from a group consisting of mucus, urine, tear fluid, spinal fluid, and amniotic fluid.

18. The method recited in claim 16, wherein the determining step comprises detecting a presence of a protein in the test fluid sample.

19. A method for detecting a presence of an antibody in a mammalian fluid sample, the method comprising the steps of:
    coating a metallic bead with an antigen;
    adding the coated bead to the test fluid sample;
    taking a transmission spectrum of the test fluid sample in at least a portion of the ultraviolet visible near-infrared range of the electromagnetic spectrum;
    comparing the test spectrum with a portion of a standard test fluid sample spectrum, the standard test fluid sample known to be free from the antibody; and determining from the comparison whether the fluid from the test sample contains an antibody to the antigen.

20. The method recited in claim 19, wherein the determining step comprises determining from a scattering analysis of the test spectrum whether an agglutination reaction has occurred among the coated beads.

21. A system for detecting a presence of and identifying an infectious disease or disorder in a mammalian blood sample comprising:

a spectrophotometer for taking a transmission spectrum of a test blood sample in at least a portion of the ultraviolet visible near-infrared range of the electromagnetic spectrum;

means for accessing a standard spectrum from a blood sample known to be free from the infectious disease or disorder means for comparing the test sample spectrum with the standard blood sample spectrum; and means for determining from the comparison whether the blood from the test sample contains the infectious disease or disorder and an identity of the infectious disease or disorder.

22. The system recited in claim 21, wherein the accessing means comprises a processor and a storage medium in electronic communication with the processor, the storage medium having stored thereon a database of standard spectra.

23. The system recited in claim 22, wherein the comparing means and the determining means comprise a software package resident on the processor having a routine for performing spectral deconvolution of the standard spectrum and the test spectrum, for identifying features of the test spectrum associated with the infectious disease or disorder.

24. The system recited in claim 22, wherein the comparing means comprises an output device in electronic communication with the processor for providing the standard spectrum and the test spectrum in visible form.

25. The system recited in claim 24, wherein the visible form comprises a co plot of the standard spectrum and the test spectrum.

26. The system recited in claim 24, wherein the output device comprises at least one of a printer and a display device.

27. The system recited in claim 24, wherein the determining means composes means for viewing the standard spectrum and the test spectrum together.

28. A system for detecting a presence of and identifying an infectious disease or disorder in a mammalian fluid sample comprising:

a spectrophotometer for taking a transmission spectrum of a test fluid sample in at least a portion of the ultraviolet visible near-infrared range of the electromagnetic spectrum;

means for accessing a standard spectrum from a like fluid sample known to be free from the infectious disease or disorder;

means for comparing the test sample spectrum with the standard fluid sample spectrum; and means for determining from the comparison whether the fluid from the test sample contains the infectious disease or disorder and an identity of the infectious disease or disorder.

* * * * *